US012215350B2

(12) United States Patent
Duggal et al.

(10) Patent No.: US 12,215,350 B2
(45) Date of Patent: *Feb. 4, 2025

(54) MONONUCLEAR CELL DERIVED NK CELLS

(71) Applicant: ImmunityBio, Inc., Culver City, CA (US)

(72) Inventors: Rohit Duggal, San Diego, CA (US); Ranjeet Sinha, San Diego, CA (US); Wenzhao Li, San Diego, CA (US); Jason Isaacson, San Diego, CA (US); Karl Marquez, San Diego, CA (US); Patrick Soon-Shiong, Culver City, CA (US)

(73) Assignee: ImmunityBio, Inc., Culver City, CA (US)

( * ) Notice: Subject to any disclaimer, the term of this patent is extended or adjusted under 35 U.S.C. 154(b) by 1387 days.

This patent is subject to a terminal disclaimer.

(21) Appl. No.: 16/796,226

(22) Filed: Feb. 20, 2020

(65) Prior Publication Data

US 2021/0009954 A1 Jan. 14, 2021

Related U.S. Application Data

(62) Division of application No. 16/505,528, filed on Jul. 8, 2019, now Pat. No. 11,453,862.

(51) Int. Cl.
| | |
|---|---|
| *C12N 5/0783* | (2010.01) |
| *C07K 14/54* | (2006.01) |
| *C07K 14/735* | (2006.01) |

(52) U.S. Cl.
CPC ........ *C12N 5/0646* (2013.01); *C12N 2500/30* (2013.01); *C12N 2501/998* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 8,926,964 B2 | 1/2015 | Hariri et al. | |
| 10,125,351 B2 | 11/2018 | Wang et al. | |
| 11,453,862 B2 * | 9/2022 | Duggal | C12N 5/0646 |
| 2012/0258085 A1 | 10/2012 | Alici | |
| 2013/0295671 A1 | 11/2013 | Deng et al. | |
| 2018/0044636 A1 | 2/2018 | Spanholtz et al. | |
| 2018/0355317 A1 | 12/2018 | Shin | |
| 2019/0023766 A1 | 1/2019 | Wong et al. | |
| 2019/0276803 A1 | 9/2019 | Shin et al. | |
| 2021/0009953 A1 | 1/2021 | Duggal et al. | |

FOREIGN PATENT DOCUMENTS

| | | |
|---|---|---|
| CN | 102428173 A | 4/2012 |
| CN | 108070556 A | 5/2018 |
| CN | 108699523 A | 10/2018 |
| EP | 2 666 466 A1 | 11/2013 |
| WO | 2010110734 A1 | 9/2010 |
| WO | 2011/068896 A1 | 6/2011 |
| WO | 2011/103882 A1 | 9/2011 |
| WO | 2012/099093 A1 | 7/2012 |
| WO | 2012/128622 A1 | 9/2012 |
| WO | 2015154012 A1 | 10/2015 |
| WO | 2015/165700 A1 | 11/2015 |
| WO | 2016/123100 A1 | 8/2016 |
| WO | 2016/205784 A1 | 12/2016 |
| WO | 2017142187 A1 | 8/2017 |
| WO | 2018/058067 A1 | 3/2018 |
| WO | 2018/071919 A1 | 4/2018 |
| WO | 2018/158350 A1 | 9/2018 |
| WO | 2018/165208 A1 | 9/2018 |
| WO | 2018/209208 A1 | 11/2018 |
| WO | 2018213828 A1 | 11/2018 |
| WO | 2019046313 A1 | 3/2019 |

OTHER PUBLICATIONS

Detela and Cattaruzzi (Human Gene Ther. 2017, 28(12): p. A93, P275) (Year: 2017).*
VivaBioCell (2021, pp. 1-6) (Year: 2021).*
VivaBioCell (2021, pp. 1-6) and VivaBioCell_NANT 001 (2021, pp. 1-13) (Year: 2021).*
Abel et al (Front. Immunol. 2018, doi: 10.3389/fimmu.2018.01869, vol. 9, article 1869, pp. 1-23) (Year: 2018).*
Angelo et al (Immunol. Res. 2015, 62: 341-356) (Year: 2015).*
Second Office Action received for Canadian Patent Application Serial No. 3,120,695 dated May 5, 2023, 5 pages.
Han et al., "IL-15:IL-15 receptor alpha superagonist complex: high-level coexpression in recombinant mammalian cells, purification and characterization", Cytokine, vol. 56, No. 3, Oct. 22, 2011, pp. 804-810.
Examination Report No. 3 received for Australian Patent Application Serial No. 2019456283 dated Apr. 17, 2023, 5 pages.
Wu, Jennifer, "IL-15 Agonists: The Cancer Cure Cytokine", Journal of Molecular and Genetic Medicine: An International Journal of Biomedical Research, vol. 7, No. 85. Oct. 28, 2012, pp. 1-6.
Lin et al., "The Common Cytokine Receptor γ Chain Family of Cytokines", Cold Spring Harbor perspectives in Biology, vol. 10, No. 9, Sep. 1, 2018, pp. 1-37.
Seay et al., "In Vivo Activation of Human NK Cells by Treatment With An Interleukin-15 Superagonist Potently Inhibits Acute in Vivo HIV-1 Infection in Humanized Mice", Journal of Virology, vol. 89, No. 12, Jun. 2015, pp. 6264-6274.

(Continued)

*Primary Examiner* — Michael Szperka
*Assistant Examiner* — Marianne Dibrino
(74) *Attorney, Agent, or Firm* — Umberg Zipser LLP

(57) ABSTRACT

Cord blood or peripheral blood NK cells are prepared from whole blood mononuclear cells without the need to isolate CD34+ hematopoietic stem cells or NK cells, and without the need for a feeder layer. Advantageously, the methods presented herein use an enrichment process that uses antiCD16 agonist antibodies, antiCD3 antibodies, and N-803. Moreover, contemplated processes are suitable for adaptation into a fully automated production process (GMP in a box).

20 Claims, 4 Drawing Sheets

(56) References Cited

OTHER PUBLICATIONS

Notice of Acceptance received for Australian Patent Application Serial No. 2019456283 dated May 24, 2023, 3 pages.
International Preliminary Report on Patentability received for PCT Application Serial No. PCT/US2019/040867 dated Jan. 20, 2022, 9 pages.
Final Office Action received for U.S. Appl. No. 16/505,528 dated Mar. 23, 2022, 22 pages.
Office Action received for Israel Patent Application Serial No. 283998 dated Jan. 13, 2022, 7 pages. (Including English Translation).
Notice of Allowance received for U.S. Appl. No. 16/505,528 dated Jul. 26, 2022, 10 pages.
Kim et al., "IL-15 superagonist/IL-15RαSushi-Fc fusion complex (IL-15SA/ IL-15RαSu-Fc; ALT-803) markedly enhances specific subpopulations of NK and memory CD8+ T cells, and mediates potent anti-tumor activity against murine breast and colon carcinomas", Oncotarget, Feb. 18, 2016, vol. 7, No. 13, pp. 16130-16145.
Li et al., "Optimized Protocols for Generation of Cord Blood derived Cytokine-induced Killer/Natural Killer Cells", Anticancer Research, 2010, vol. 30, pp. 3493-3500.
Hu et al., "Discovery of a novel IL-15 based protein with improved developability and efficacy for cancer immunotherapy", Scientific Reports, 2018, vol. 8, No. 7675, pp. 1-11.
Final Office Action received for U.S. Appl. No. 16/505,528 dated Nov. 4, 2020, 23 pages.
Extended European Search Report received for EP Patent Application Serial No. 19936966.1 dated Mar. 22, 2022, 10 pages.
Lee et al., "Expansion of cytotoxic natural killer cells using irradiated autologous peripheral blood mononuclear cells and anti-CD16 antibody", Scientific Reports, vol. 7, Article 11075, Sep. 11, 2017, pp. 1-13.
Non-Final Office Action received for U.S. Appl. No. 16/505,528 dated Jun. 24, 2021, 18 pages.
Iyer et al., "Industrializing Autologous Adoptive Immunotherapies: Manufacturing Advances and Challenges", Frontiers in Medicine, May 2018, vol. 5, No. 150, pp. 1-9.
Detela et al., "A novel automated, closed system solution for simple, de-risked and cost-effective antologous ATMP manufacturing: the NANT 001 bioreactor, Selected Poster Presentations", Human Gene Therapy, 2017, vol. 28, No. 12, p. A93.
VivaBioCell (Year: 2021), 6 pages.
Non-Final Office Action received for U.S. Appl. No. 16/505,528 dated Dec. 8, 2021, 20 pages.
NANT 001, VivaBioCell, 2021, pp. 1-13.
Galatiuc et al., "Natural Killer (NK) Activity in Human Responders and Nonresponders to Stimulation by anti-CD16 Antibodies", Cellular immunology, 1995, vol. 163, pp. 167-177.
Wu et al., "Automated Cell Expansion: Trends & Outlook of Critical Technologies, Critical Role of Automation in the Manufacture of Cell & Gene Therapies", Cell and Gene Therapy, 2018, pp. 843-863.
"NCI Drug Dictionary", National Cancer institute, 2020, URL: cancer.gov/publications/dictionaries/cancer-drug/def/751380, 1 page.
Otegbeye et al., "The IL-15 Super-Agonist ALT-803 Promotes Superior Activation and Cytotoxicity of Ex Vivo Expanded NK Cells Against AML", Blood, 2015, vol. 126, No. 23, pp. 1-7.
Non-Final Office Action received for U.S. Appl. No. 16/505,528 dated Apr. 29, 2020, 105 pages.
International Search Report and Written Opinion received for PCT Application Serial No. PCT/US2019/040867 dated Apr. 8, 2020, 11 pages.
Fenerty et al., "Immunotherapy utilizing the combination of natural killer and antibody dependent cellular cytotoxicity (ADCC)-mediating agents with poly (ADP-ribose) polymerase (PARP) inhibition", Journal for Immunotherapy of Cancer, 2018, vol. 6, No. 133, pp. 1-14.
Examination Report No. 1 received for Australian Patent Application Serial No. 2019456283 dated Sep. 27, 2022, 8 pages.
Felices et al., "IL-15 super-agonist (ALT-803) enhances natural killer (NK) cell function against ovarian cancer", Gynecol Oncol., vol. 145, No. 3, Jun. 2017, pp. 453-461.
Decision to Grant a Patent received for Japanese Patent Application Serial No. 2021-527968 dated Dec. 20, 2022, 5 pages. (Including English Translation).
Rosario et al., "The IL-15-based ALT-803 complex enhances FcγRIIIa-triggered NK cell responses and in vivo clearance of B cell lymphomas", Clin Cancer Res., vol. 22, No. 3, Feb. 1, 2016, pp. 596-608.
Examination Report No. 2 received for Australian Patent Application Serial No. 2019456283 dated Feb. 13, 2023, 4 pages.
Office Action received for CN Patent Application Serial No. 201980078702.2 dated Jun. 25, 2024, 26 pages (including English translation).
Office Action received for KR Patent Application Serial No. 10-2021-7018216 dated May 29, 2024, 08 pages (including English translation).

* cited by examiner

MONONUCLEAR CELL DERIVED NK CELLS

This application is a divisional application of copending US application with the Ser. No. 16/505,528, which was filed Jul. 8, 2019.

FIELD OF THE INVENTION

The present disclosure relates to compositions, methods, and devices to generate and cultivate immune competent cells, especially as it relates to cord blood (CB) or peripheral blood (PB) NK cells from whole blood.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Natural killer (NK) cells constitute a group of innate immune cells, which are often characterized as cytotoxic lymphocytes that exhibit antibody dependent cellular toxicity via target-directed release of granulysin and perforin. Most NK cells have a specific cell surface marker profile (e.g., $CD3^-$, $CD56^+$, $CD16^+$, $CD57^+$, $CD8^+$) in addition to a collection of various activating and inhibitory receptors. While more recently NK cells have become a significant component of certain cancer treatments, generation of significant quantities of NK cells (and especially autologous NK cells) has been a significant obstacle as the fraction of NK cells in whole blood is relatively low.

To obtain therapeutically meaningful quantities of NK and NK-like cells, NK cells can be generated from various precursor cells. For example, various stem cell factors (SCF), FLT3 ligand, interleukin (IL)-2, IL-7 and IL-15 have been reported in various in vitro approaches to induce and expand cord blood-derived cytokine-induced killer (CIK) cells (*Anticancer Research* 30: 3493-3500 (2010)). Similarly, $CD34^+$ hematopoietic cells can be exposed to IL-12 and other agents as is reported in US 2018/0044636. In still other approaches, human hemangioblasts were sequentially exposed to two different cytokine cocktails as described in WO2011/068896, and different cytokine cocktails were used with post-embryonic hematopoietic stem cells as taught in WO2012/128622. While at least some of these methods provide a significant n-fold expansion of NK cells, methods and reagents for such expansion are both time and resource demanding. Still further, it should be noted that many of the known methods also require NK cell culture on a feeder cell layer, which is often problematic from a technical and a regulatory perspective.

In more simplified methods, acute myeloid leukemia (AML) cells can be exposed to TpoR agonists to so induce the AML cells to form NK cells. However, such approach is likely not viable as a source for therapeutic cell preparations.

Alternative methods have also relied on culturing peripheral blood cells in the presence of various interleukins, stem cell factors, and FLT3 ligands as is disclosed in WO 2011/103882. In yet another method, US 2013/0295671 teaches methods of stimulating already existing NK cells with anti-CD16 and anti-CD3 antibodies along with cytokines. While procedurally simpler, such methods still require elaborate manipulation of the cells and add significant costs due to the specific reagent required.

In still further known methods, U.S. Pat. No. 10,125,351 describes use of cord blood or peripheral blood as a source of cells that are subject to density gradient separation to isolate nucleated cells that are then cultivated with a medium that contains interferon, interleukin, a CD3 antibody and human albumin. Most advantageously, such method is amenable to perfusion culture in a bioreactor and as such significantly reduces operational difficulties. Unfortunately, however, the yield of NK cells is relatively low.

Thus, even though various methods of generating significant quantities of NK cells are known in the art, all or almost all of them suffer from various disadvantages. Consequently, there is a need to provide improved systems and methods that produce significant quantities of NK cells, and especially autologous NK cells. Moreover, improved systems and methods will also allow for automation of cell culture and will have substantially reduced reagent requirements to render such methods clinically and commercially viable.

SUMMARY OF THE INVENTION

The inventors have discovered compositions, methods, and devices that enable generation and expansion of NK cells in a conceptually simple and efficient manner. Advantageously, NK cells can be generated from blood mononuclear cells (MNCs) obtained from cord or whole blood without isolating either $CD34^+$ hematopoietic stem cells (HSC) or NK cells, and without the use of a feeder layer, preferably by an enrichment process that uses N-803 and optionally an anti-CD16 agonist antibody and an anti-CD3 antibody.

In one aspect of the inventive subject matter, the inventors contemplate a method of producing NK cells that includes a step of isolating from a biological fluid a mixture of mononuclear cells, a step of contacting the mixture of the mononuclear cells with an anti-CD16 antibody and N-803 to activate NK cells, and another step of sequentially feeding the activated NK cells with a medium containing N-803.

In most typical examples, the step of isolating the mixture of the mononuclear cells is performed using density gradient centrifugation, and/or the biological fluid is whole blood or cord blood. Therefore, the mixture of mononuclear cells will generally include T cells, NK cells, NKT cells, and double negative (DN) T cells. While not categorically excluded, it is generally preferred that the mixture of mononuclear cells is not further processed to enrich NK cells.

With respect to contemplated anti-CD16 antibodies it is generally preferred that the antibody is a monoclonal antibody with specificity to human CD16. Most typically, the anti-CD16 antibody is present at a concentration of between 0.05-0.5 mcg/ml, and/or the N-803 is present at a concentration of between 0.1-1.0 nM. Where desired, contemplated methods may also include a step of contacting the mixture further includes contacting the mixture of the mononuclear cells with an anti-CD3 antibody (e.g., at a concentration of between 0.1-1.0 ng/ml).

In some embodiments, the mixture of the mononuclear cells contains about $100\text{-}500 \times 10^6$ cells, and/or the step of contacting the mixture is performed in a volume of between about 100-300 ml or at a cell density of about $1\times10^6$ cells/ml. Preferably, but not necessarily, the medium containing N-803 comprises human AB serum and/or NK MACS™ medium (commercially available from Mileny Biotech, Friedrich-Ebert-Straße 68, 51429 Bergisch Gladbach, Germany) and hydrocortisone (0.1-5 uM). Moreover, it is contemplated that the step of sequentially feeding is performed about every 72 hours, and/or that the step of sequentially feeding is performed until a total cell number of about $0.5-5.0\times10^9$ cells is reached. Furthermore, the step of sequentially feeding the activated NK cells may be performed in single container and the step of contacting the mixture of the mononuclear cells may be performed in the same container.

In other embodiments, the step of sequentially feeding the activated NK cells is performed until NK cells are enriched to an at least 100-fold expansion, and/or until NK cells constitute at least about 80% or at least about 90% of all live cells.

Therefore, and viewed form a different perspective, the inventors also contemplate a method of expanding NK cells from a mixture of mononuclear cells that includes a step of providing a mixture of the mononuclear cells that contains equal or less than 5% NK cells. In another step, the mixture of the mononuclear cells is then contacted with an anti-CD16 antibody and N-803 to activate NK cells, and in a further step the activated NK cells are fed with a medium containing N-803.

Preferably, but not necessarily, the mixture of the mononuclear cells is obtained from whole blood or cord blood, or the mixture of the mononuclear cells is obtained from an MHC-matched autologous source relative to an individual that receives the NK cells. In typical examples, the mixture of the mononuclear cells that contains equal or less than 3% NK cells, and/or may further comprise T cells, NKT cells, and DN cells. With respect to the medium, anti-CD16 antibody, the N-803, and the anti-CD3 antibody, the same considerations as noted above apply.

Additionally, it is contemplated that the step of feeding comprises sequentially feeding at an interval of about every 72 hours, that the step of feeding is performed until a total cell number of about $0.5-5.0\times10^9$ cells is reached, and/or that the step of feeding the activated NK cells is performed until NK cells are enriched to an at least 100-fold expansion. In further embodiments, it is contemplated that the step of feeding the activated NK cells is performed in an automated manner, preferably in a single container.

Thus, in yet another aspect of the inventive subject matter, the inventors also contemplate a method of expanding NK cells in an automated bioreactor. Such method will typically include a step of incubating a mixture of mononuclear cells in an activation medium containing N-803 and an anti-CD16 antibody for a time sufficient to activate NK cells, wherein the mixture of mononuclear cells is contained in a cell culture container while incubating the mixture. In another step, growth of the cells is measured while the cells are in the container, and the cells are automatically fed with a medium containing N-803 according to a predetermined schedule and/or a result from the step of measuring growth of the cells. In still another step, feeding the cells is terminated according to a predetermined schedule and/or a result from the step of measuring growth of the cells.

For example, suitable containers will have a volume of between about 200 ml and about 2,500 ml, and/or the step of measuring growth of the cells is performed through a wall of the container (e.g., using optical measurements). Most preferably, the activation medium contains N-803 at a concentration of between 0.1-1.0 nM and an anti-CD16 antibody at a concentration of between 0.05-0.5 mcg/ml. In other examples, the medium containing N-803 contains N-803 at a concentration of between 0.1-1.0 nM. Most typically, the time sufficient to activate NK cells is between 24 hours and 96 hours, and the cells are fed until a total cell number of about $0.5-5.0\times10^9$ cells is reached, and/or until NK cells are enriched to an at least 100-fold expansion.

In still another aspect of the inventive subject matter, the inventors also contemplate a cell culture container (e.g., having a volume of between about 200 ml and about 2,500 ml) that contains a medium with distinct types of immune competent cells. Most preferably, the medium contains NK cells in an amount of at least 80% of all live cells, NKT cells in an amount of equal or less than 10% of all live cells, T cells an amount of equal or less than 5% of all live cells, and DN T cells an amount of equal or less than 3% of all live cells. Preferably, at least one wall of the container has an optically transparent portion, and/or the NK cells are present in an amount of at least about 90% of all live cells.

Various objects, features, aspects, and advantages will become more apparent from the following detailed description of preferred embodiments, along with the accompanying drawing in which like numerals represent like components.

DETAILED DESCRIPTION

With the continuously increasing use of immune therapies in the treatment of cancer, production of sufficient quantities of NK cells, and especially autologous NK cells as therapeutic entities has become critical. Unfortunately, many of the current methods require use of feeder layers or differentiation of isolated CD34+ hematopoietic stem cells (HSCs), which is both time and resource intensive. Moreover, due to the various manipulation steps needed, such methods typically require human interaction and are prone to contamination.

Figure 1:
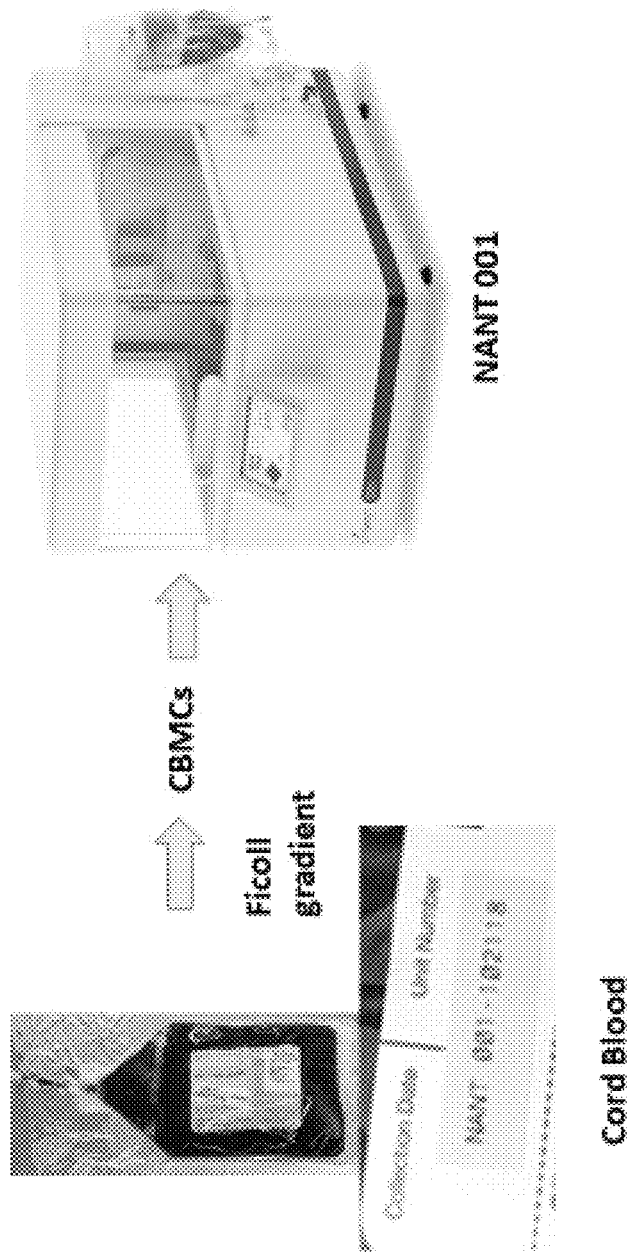
FIG. 1 depicts an exemplary schematic illustrating a process starting from cord blood through isolation of CBMCs that then make up the seed for the enrichment/expansion of NK cells.

In an effort to improve production methods for NK cells, the inventors have now discovered various systems, compositions, and methods to generate therapeutically meaningful quantities (e.g., at least $0.5\times10^9$ NK cells) from a biological fluid containing mononuclear cells (e.g., whole blood, cord blood) in a simple and effective manner that can even be fully automated once the mononuclear cells are obtained as is schematically illustrated in FIG. 1. Preferably, the bioreactor is a self-contained unit and will have a central processor and memory on board to execute a programmable protocol for various activities (e.g., operation of pumps for fluid movements, temperature and gas regulation, image processing, etc.) and to generate regulatory-ready reports, as well as a microscope (or other optical unit) for monitoring the cell culture.

For example, in one process contemplated herein, whole peripheral blood or cord blood is used as a starting material that is processed to obtain mononuclear cells. Most typically, processing can be done using conventional density gradient centrifugation (e.g., using FICOLL® Paque Plus™ (a hydrophilic soluble polysaccharide, density 1.077 g/mL), commercially available from GE Lifesciences). Once the mononuclear cells are separated from the centrifuge tube, the cells are washed and re-suspended in an activation medium (e.g., NK MACS supplemented with 10% human AB serum). The activation medium further comprises N-803 at a concentration of about 0.4 nM, and an anti-CD16 antibody at a concentration of about 1.0 mcg/ml.

Figure 2:
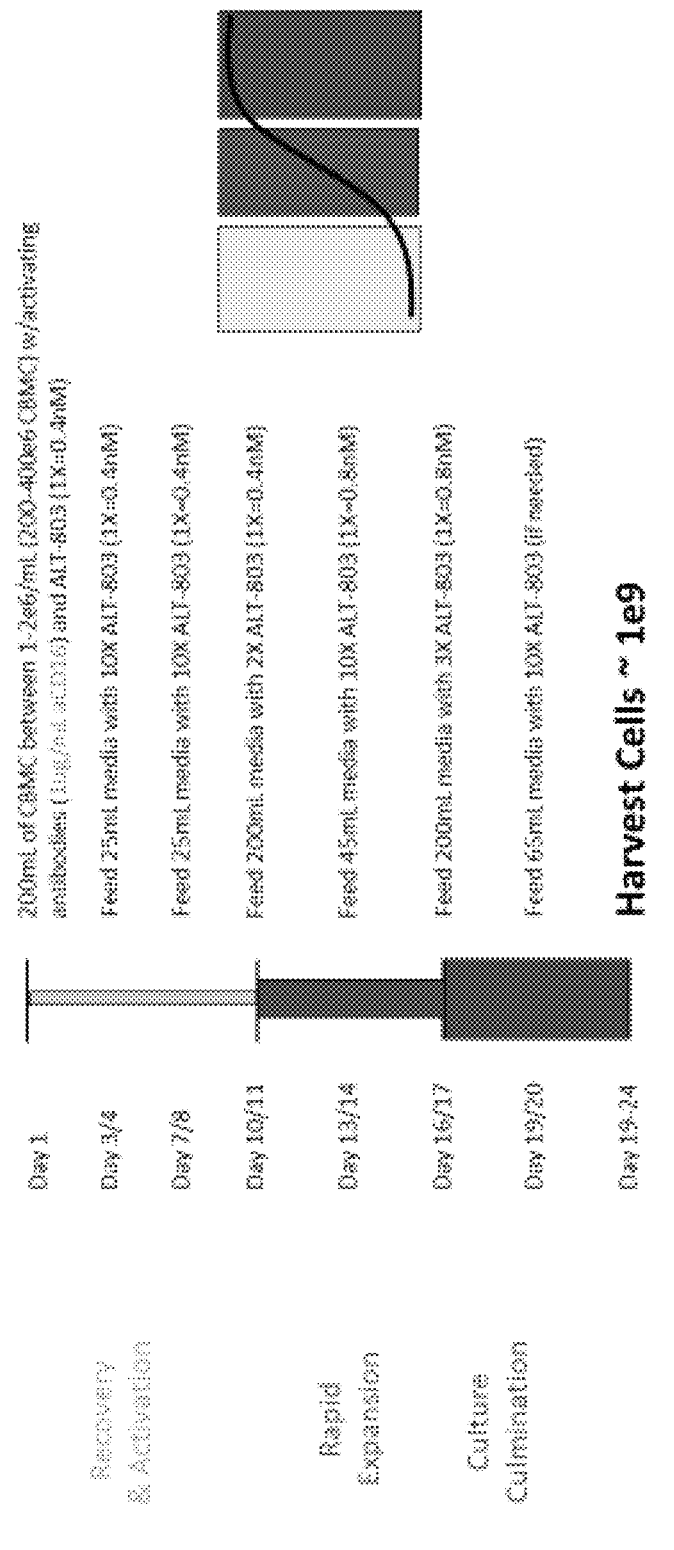
FIG. 2 depicts exemplary details of a representative process in an automated environment ('GMP in a box') and the schedule of addition of various ingredients.
Figure 3:
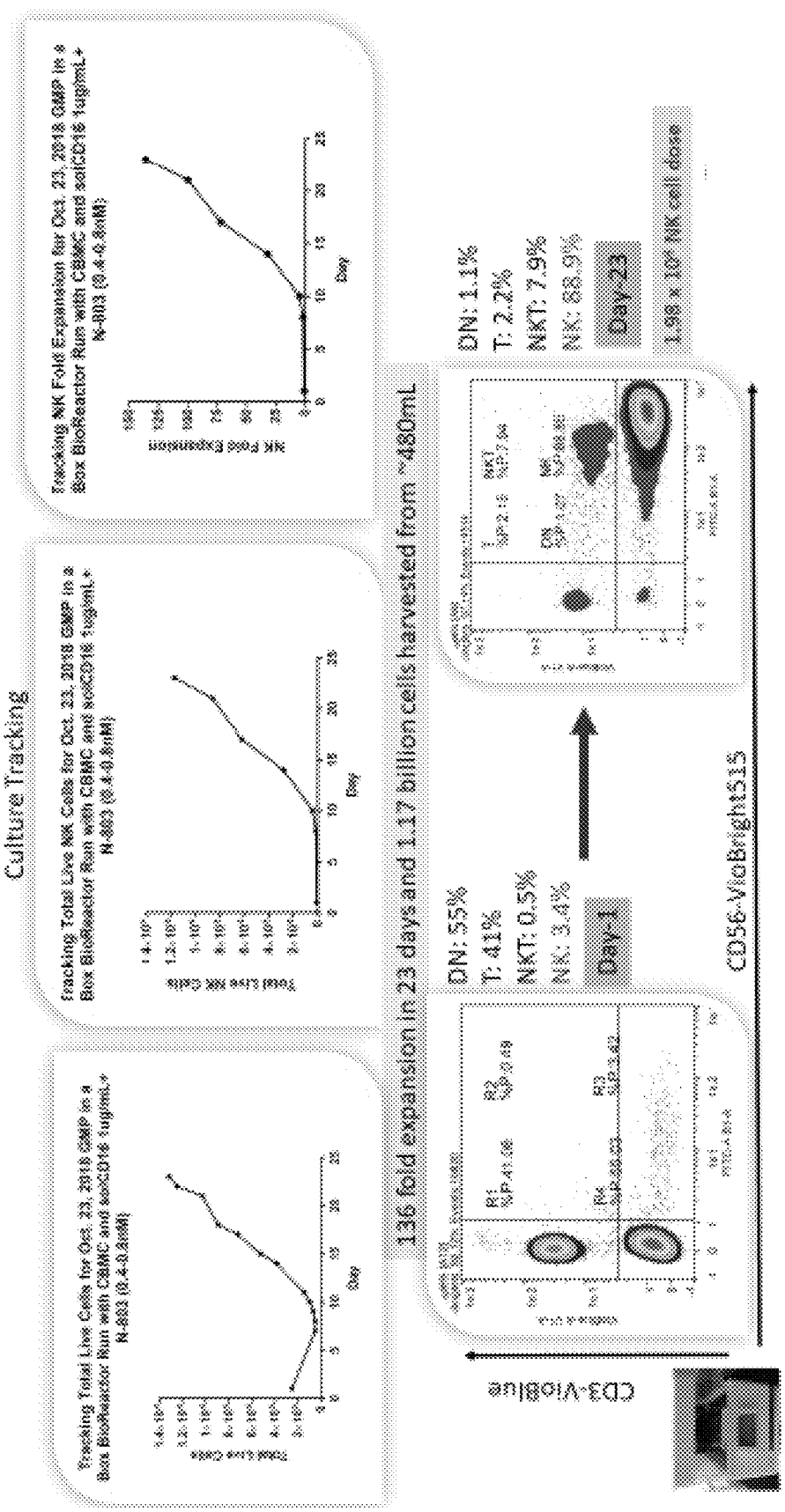
FIG. 3 depicts exemplary results for enrichment kinetics of the process of FIG. 2 for NK cells by number and selected flow cytometry properties.
Figure 4:
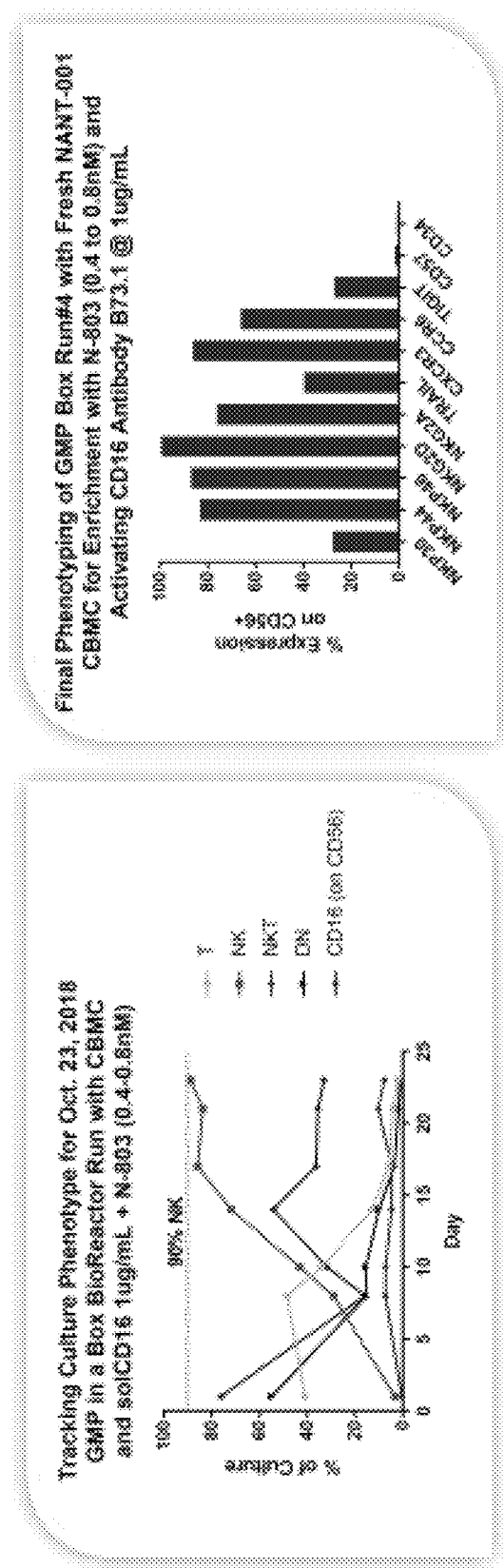
FIG. 4 depicts exemplary results for kinetics of various cell populations of the process of FIG. 2 along results for with marker expression, especially significant expression of the majority of NK activation receptors.

Most typically, the mononuclear cells have a density of $1\text{-}2 \times 10^6$ cells/ml in a total volume of about 200 ml, and the cells and medium are in a single container. After about 3-4 days, the cells are fed with fresh medium containing N-803, and further feed cycles are performed about every three days through recovery, rapid expansion, and culture culmination as exemplarily shown in FIG. 2. Cells are harvested upon reaching a desired quantity, typically about $0.5\text{-}5.0 \times 10^9$ total cells and/or upon reaching a desired expansion (e.g. at least 100-fold expansion). Notably, despite the apparent simplicity, the so obtained cell culture contains after about three weeks more than about 85% NK cells, with less than about 8% NKT cells, and with less than about 2.5% T cells, and less than about 1.2% double negative (DN) T cells. Moreover, it should be recognized that the entire culture process may be performed in a single container within a self-contained bioreactor, which substantially reduces risk of contamination and eliminates reagent and cell handling during the cultivation step. FIG. 3 depicts exemplary results for an NK production that yielded an about 136-fold expansion of NK cells in 23 days with a total of $1.17 \times 10^9$ cells harvested from a final volume of about 480 ml. FIG. 4 depicts further experimental data that illustrate cell composition over time tracking T cells, NK cells, NKT cells, DN cells (along with CD16 results; left panel). Results for the final phenotyping for the cells harvested in the process of FIG. 2 and FIG. 3 are shown in the right panel of FIG. 4. As can be readily seen, the detected markers were indicative of NK cells.

With respect to suitable biological fluids, it is generally contemplated that the fluids could be autologous relative to the individual that will receive the NK cells isolated in the methods presented herein. Therefore, especially preferred biological fluids include fresh whole blood, cord blood (frozen or fresh), and cells separated in a leukapheresis procedure. However, it should be appreciated that the biological fluid may also be any fluid that contains NK cells (typically among other cell types). For example, suitable alternative biological fluids include whole blood from allogenic donors, which may or may not be matched for a compatible MHC type. Therefore, samples in a blood bank that approach expiration date are deemed suitable for use, as well as freshly donated whole or stored cord blood by an individual other than the NK cell recipient.

Likewise, it should be noted that the manner of isolating or enriching mononuclear cells may vary considerably, and the person of ordinary skill in the art will be readily apprised of the most suitable methods of isolation and enrichment. For example, where the biological fluid is whole blood or cord blood, it is preferred that the fluid is processed via gradient density centrifugation using any suitable medium (e.g., FICOLL® Hypaque). Alternatively, mononuclear cells may be obtained directly from the patient by leukapheresis, or the biological fluid may be subjected to removal of red blood cells using antibodies. In still further methods, mononuclear cells may be isolated using magnetic bead separation where the beads are coated or otherwise coupled to antibodies binding the mononuclear cells.

Likewise, it should be recognized that the particular nature of the medium for activation and feeding need not be limited to NK MACS medium, but that all media known to support growth of NK cells are deemed suitable for use herein. Most preferably, however, defined media are used and may be supplemented with human AB serum.

Activation of the NK cells in the mixture of mononuclear cells is preferably performed with a combination of an anti-CD16 antibody and N-803, and optionally an anti-CD3 antibody. There are various sources for anti-CD16 antibodies known in the art/commercially available, and particularly preferred anti-CD16 antibodies have agonist (activating) activity and are specific to human CD16. However, activators other than anti-CD16 antibodies are also deemed suitable for use herein include anti-CD16 antibody fragments and fusion proteins with anti-CD16 antibody fragments. Additionally, or alternatively, contemplated activators also include CD314 or NKG2D, the natural cytotoxicity receptors CD335 (NKp46), CD336 (NKp44) and CD337 (NKp30), CD226 (DNAM-1), CD244 (2B4), members of the CD158 or killer immunoglobulin-like receptor (KIR) family that carry a short cytoplasmic tail (KIR2DS and KIR3DS) and CD94/NKG2C, among others.

Concentrations of the anti-CD16 antibody will typically follow those already known in the art for activation of NK cells. Therefore, suitable concentrations for anti-CD16 antibodies will be between about 0.01-5.0 mcg/ml, and more typically between about 0.01-0.3 mcg/ml, or between about 0.05-0.5 mcg/ml, or between about 0.1-1.0 mcg/ml, or between about 1.0-5.0 mcg/ml. With respect to the duration of exposure to the anti-CD16 antibody it is generally contemplated that the mixture of mononuclear cells is exposed to only a single, two, or there doses of the anti-CD16 antibody, most typically when the mononuclear cells are isolated and contacted with the activation medium for the first (and/second, and/or third) time. The person of ordinary skill in the art will be readily able to recognize proper schedule and dosage to achieve NK cell activation. Most typically, exposure of the mononuclear cells to the anti-CD16 antibody is contemporaneous with exposure of the mononuclear cells with the N-803. However, in less preferred embodiments, exposure of the mononuclear cells to the anti-CD16 antibody is sequentially to exposure of the mononuclear cells with the N-803 (with exposure of the mononuclear cells to the anti-CD16 antibody first being the preferred sequence).

Where desired, activation may also include contacting the cells with anti-CD3 antibody, typically at the same time of contacting the cells with anti-CD16 antibody. As noted above, concentrations of the anti-CD3 antibody will typically follow those already known in the art for activation of NK cells. Therefore, suitable concentrations for anti-CD3 antibodies will be between about 0.01-10.0 ng/ml, and more typically between about 0.01-0.1 ng/ml, or between about 0.1-0.5 ng/ml, or between about 0.3-1.0 ng/ml, or between about 1.0-5.0 ng/ml. Likewise, with respect to the duration of exposure to the anti-CD3 antibody it is generally contemplated that the mixture of mononuclear cells is exposed to only a single, two, or there doses of the anti-CD3 antibody, most typically when the mononuclear cells are isolated and contacted with the activation medium for the first (and/second, and/or third) time. The person of ordinary skill in the art will be readily able to recognize proper schedule and dosage to achieve NK cell activation.

With respect to N-803 it is contemplated that N-803 (an IL-15N72D:IL-15RαSu/IgG1 Fc complex with human sequences; see US 2019/0023766, commercially available from ImmunityBio) is preferred as an agent in the activation and feed medium. However, various alternative agents with IL-15 activity are also deemed suitable for use herein. In this context, and without wishing to be bound by any theory or hypothesis, the inventors contemplate that N-803 enables growth and expansion of the NK cells by virtue of continuous signaling. In contrast, IL-15 as isolated cytokine has a very short lifespan and signaling activity is typically very short. This, where IL-15 as isolated cytokine is added to a growth medium, the signaling will be pulsed or intermittently. In contrast, where N-803 is provided, stability of IL-15 is dramatically extended and signaling is deemed continuous. Moreover, it should be recognized that N-803 also provides a physiological context (i.e., IL-15 R-alpha chain) and a N72D form that acts as a super agonist. Therefore, any stabilized IL-15 compound is also expressly deemed suitable for use herein. In yet further contemplated aspects, IL-15 (recombinant, recombinantly expressed, or isolated) and/or N-803 may be at least in part replaced or supplemented by TxM type fusion protein complexes, especially preferred fusion protein complexes are described in WO 2018/165208, which is incorporated by reference herein. For example, contemplated TxM type fusion protein complexes will include at least one additional cytokine selected from the group consisting of IL-7, IL-18, and IL-21. Therefore, and among other suitable choices, contemplated TxM fusion complexes include an IL-18/IL-7 TxM and/or IL-18/IL-21 TxM.

For example, all compounds and complexes that effect IL-15 signaling are deemed suitable for use herein so long as such compounds and complexes have a serum half-life that is longer than isolated/recombinant and purified IL-15 alone. Moreover, it is generally preferred that the stabilized IL-15 compounds will include at least portions of human sequences for IL-15 and/or IL-15 Rα. For example, suitable compounds include P22339 (a complex of IL-15 and the Sushi domain of IL-15Rα chain with a disulfide bond linking the IL-15/Sushi domain complex with an IgG1 Fc to augment its half-life; see *Nature, Scientific Reports* (2018) 8:7675), and XmAb24306, which is a IL-15/IL-15Rα-Fc heterodimer (see e.g., WO 2018/071919).

In further especially contemplated embodiments, the mixture of mononuclear cells is, after isolation from the biological fluid, placed into a cell culture container together with the medium containing the anti-CD16 (and optionally anti-CD3) antibody and N-803 to activate the NK cells. Most preferably, the container is a cell culture flask with at least one wall (or portion thereof) that is transparent to light such that cell shape, staining, and/or growth can be observed with a microscope or other optical instrument. Thus, it should be noted that the cells can be continuously or periodically monitored in a bioreactor, and so obtained measurements (e.g., cell size, cell number, cell distribution, etc.) can be used to trigger or modify an automated feeding schedule in a control unit that is logically coupled to the bioreactor. Most typically, and as shown in FIG. 2, feeding fresh medium with N-803 can be performed using a pre-defined schedule, typically every three days, where preferably each feeding will include N-803 to maintain continuous signaling. While the specific volumes shown in FIG. 2 are suitable for expanding the NK cells to cell densities consistent with cell growth, it should be appreciated that the volumes may be adjusted to accommodate particular growth patterns. To that end, it should also be appreciated that the feeding may be continuously or that predetermined volumes may be changed in response to the growth kinetic observed in the container.

In most cases, the yield of the NK cells at the end of the cultivation will be typically at least 80%, or at least 82%, or at least 85%, or at least 88%, or at least 90%, or at least 92%, or at least 94% of all live cells with the remainder being NKT cells, DN T cells, and T cells. For example, remaining NKT cells will typically be equal or less than 10%, or equal or less than 8%, or equal or less than 7%, or equal or less than 6% of all live cells, while remaining T cells will typically be equal or less than 5%, or equal or less than 4%, or equal or less than 3%, or equal or less than 2% of all live cells, and remaining DN T cells will typically be equal or less than 3%, or equal or less than 2%, or equal or less than 1.5%, or equal or less than 1% of all live cells.

Therefore, and viewed from a different perspective, it should be appreciated that the systems and methods contemplated herein are capable of remarkably high expansion of NK cells, and typical expansions are at least 80-fold, or at least 100-fold, or at least 120-fold, or at least 130-fold, or at least 140-fold with respect to the number of NK cells originally present in the mixture of mononuclear cells. Such expansion is particularly notable in view of the very simple manner of activation and cultivating (one-pot process). Indeed, once the mixture of mononuclear cells is placed into the cell culture container, the entire process con continue within the same container and will be sustained by addition of media only as schematically shown in FIG. 2. Thus, complex handling and expensive reagents are entirely avoided, and the risk for contamination is significantly reduced.

While not limiting to the inventive subject matter, it is therefore contemplated that the NK cells are expanded and/or activated in a culture environment that allows for continuous monitoring, continuous management of $CO_2$ and $O_2$ levels, and continuous monitoring to detect cell density (e.g., confluence). Among other options for such environments, especially preferred environments are automated cell culturing and harvesting devices as are described, for example, in WO 2015/165700. Such 'GMB-in-a-box' systems beneficially allow control over feeding schedules, gas control, allow for real-time detection of cell density, growth (kinetics) and cell health, as well as dramatically reduce the possibility of contamination due to significantly reduced handling requirements.

In still further contemplated aspects, it should be noted that the systems and methods presented herein advantageously also allow generation of $CD56^{dim}$ and $CD56^{bright}$ NK cells, particularly where the NK cells are generated from peripheral blood. Depending on further culture conditions, $CD56^{bright}$ NK cells may then differentiate to $CD56^{dim}$ cells. Such distinct NK cell populations can then be employed as for distinct therapeutic options due to their distinct maturation and cytotoxicity profile. Additionally, it should be appreciated that the compositions, systems and methods will also be suitable to generate NKT cells upon proper stimulation and culture.

EXAMPLES

In view of the above, and as provided in more detail below, one exemplary method entailed isolating CBMCs or PBMCs by a single FICOLL® centrifugation step, which was followed by incubation of the cells with about 0.4 nM N-803 and about 0.1 mcg/ml of an anti-CD16 antibody (e.g., clone B73.1, commercially available from BD Biosciences), and optionally about 0.5 ng/ml of an anti-CD3 antibody in NK MACS media with 10% human AB serum. Typically 150 mL of CBMCs at a million cells/ml were used as the starting material with above reagents. Media was used for dilution with N-803 twice a week with a regimen of a 1:2 and 1:10 compared to existing volume with corresponding concentration of N-803 for a final concentration of 0.4 nM.

Materials: MNCs from Cord and Peripheral Blood, anti-CD16 antibody, BD bioscience San Diego CA; NK MACS medium with NK supplement, staining antibodies for phenotyping (aCD3, aCD16, aCD56, aNKp30, aNKp44, aNKp46, aNKG2A, aNKG2D, aTIGIT, aCD34, aTRAIL, aCD57, aCXCR3, and aCCR5), Miltenyi Biotec San Diego, CA; Human AB serum, Access Biologicals, San Diego CA; N-803, GMP in a Box kit, Nantbio Inc Culver City CA.

Methods: MNCs were freshly isolated from cord blood or peripheral blood. It was washed twice with complete NKMACS medium (NKMACS+Supplements+10% hu-AB-serum). MNCs were suspended in 150 mL of medium with density of 1×10^6 cell/mL. 150 mL cell suspension was supplemented with aCD16 antibody (1 mcg/mL) and N-803 (0.4 nM). Further GMP kit was installed in the box and protocol uploaded through VivaBio web portal. Cells suspension with complete cytokine and antibody were transferred to cell bag, and 150 mL cell suspension was injected through cell injection port in Box-kit. GMP Box started imaging and cells were propagated according to steps written in protocol as mentioned in FIG. 2. Cells in the box were supplemented with 10× cytokine medium or with 2× cytokine medium in alternate fashion as described in FIG. 2. NK enrichment (phenotype for CD3, CD56, and CD16 expression) and cell health (cell number, viability, and cell density) were monitored regularly and plotted in graph as in FIG. 3 and FIG. 4a. Cells were harvested after enrichment from the box and measured for the expression of NK cell based receptors for its complete characterization as in FIG. 4.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the cells or exosomes are administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of expanding NK cells from a mixture of mononuclear cells, the method comprising:
   providing in a container a mixture of the mononuclear cells that contains equal or less than 5% NK cells;
   contacting the mixture of the mononuclear cells with an anti-CD16 antibody and N-803 to activate NK cells; and
   feeding in the same container the activated NK cells with a medium containing N-803 until the activated NK cells constitute at least about 80% of all live cells or until the activated NK cells are enriched to an at least 80-fold expansion.

2. The method of claim 1 wherein the mixture of the mononuclear cells is obtained from whole blood or cord blood.

3. The method of claim 1, wherein the mixture of the mononuclear cells contains equal or less than 3% NK cells.

4. The method of claim 1, wherein the anti-CD16 antibody is present at a concentration of between 0.05-0.5 mcg/ml.

5. The method of claim 1, wherein the N-803 is present at a concentration of between 0.1-1.0 nM.

6. The method of claim 1, wherein the step of contacting the mixture further includes contacting the mixture of the mononuclear cells with an anti-CD3 antibody.

7. The method of claim 6, wherein the anti-CD3 antibody is present at a concentration of between 0.1-1.0 ng/ml.

8. The method of claim 1, wherein the medium containing N-803 comprises human AB serum.

9. The method of claim 1, wherein the step of feeding comprises sequentially feeding at an interval of about every 72 hours.

10. The method of claim 1, wherein the step of feeding is performed until a total cell number of about 0.5-5.0×10^9 cells is reached.

11. The method of claim 1, wherein the step of feeding the activated NK cells is performed until NK cells are enriched to an at least 100-fold expansion.

12. The method of claim 1, wherein the step of feeding the activated NK cells is performed in an automated manner.

13. A method of expanding NK cells in an automated bioreactor, the method comprising:
incubating a mixture of mononuclear cells in an activation medium containing N-803 and an anti-CD16 antibody for a time sufficient to activate NK cells;
wherein the mixture of mononuclear cells is contained in a cell culture container while incubating the mixture;
measuring growth of the cells while the cells are in the container; automatically feeding the cells using a medium containing N-803 until the activated NK cells constitute at least about 80% of all live cells or until the activated NK cells are enriched to an at least 80-fold expansion, wherein the feeding is controlled by a predetermined schedule and/or a result from the step of measuring growth of the cells;
terminating feeding the cells wherein the terminating is controlled by a predetermined schedule and/or a result from the step of measuring growth of the cells.

14. The method of claim 13, wherein the container has a volume of between about 200 ml and about 2,500 ml.

15. The method of claim 13, wherein the step of measuring growth of the cells is performed through a wall of the container.

16. The method of claim 13, wherein the activation medium contains N-803 at a concentration of between 0.1-1.0 nM and the anti-CD16 antibody at a concentration of between 0.05-0.5 mcg/ml.

17. The method of claim 13, wherein the time sufficient to activate NK cells is between 24 hours and 96 hours.

18. The method of claim 13, wherein the medium containing N-803 contains N-803 at a concentration of between 0.1-1.0 nM.

19. The method of claim 13, wherein the cells are fed until a total cell number of about $0.5\text{-}5.0\times10^9$ cells is reached.

20. The method of claim 13, wherein the cells are fed until NK cells are enriched to an at least 100-fold expansion.

* * * * *